United States Patent [19]

Woo

[11] 3,960,837
[45] June 1, 1976

[54] POLYAMINE COMPOUNDS AND METHODS FOR THEIR PRODUCTION
[75] Inventor: Peter W. K. Woo, Ann Arbor, Mich.
[73] Assignee: Parke, Davis & Company, Detroit, Mich.
[22] Filed: Sept. 6, 1974
[21] Appl. No.: 503,991

[52] U.S. Cl............................ 260/210 AB; 424/180
[51] Int. Cl.² .................... C07H 5/06; C07H 15/22
[58] Field of Search................... 260/210 AB, 210 R

[56] References Cited
UNITED STATES PATENTS

| | | | |
|---|---|---|---|
| 3,541,078 | 11/1970 | Woo et al. | 260/210 R |
| 3,753,973 | 8/1973 | Umezawa et al. | 260/210 K |
| 3,784,541 | 1/1974 | Culbertson et al. | 260/210 R |

OTHER PUBLICATIONS

Ellis, "Hydrogenation of Organic Substances" Van Nostrand Co., 1930, p. 197.
Wagner and Zook, "Syn. Org. Chemistry" Wiley and Sons, Inc., 1953, p. 171.

Primary Examiner—Johnnie R. Brown
Assistant Examiner—Cary Owens

[57] ABSTRACT

O-2,6-Diamino-2,3,4,6-tetradeoxy-α-D-erythro-hexopyranosyl-(1 → 4)-O-[5-amino-5-deoxy-β-D-xylofuranosyl-(1 → 5)]-N¹-[(S)-4-amino-2-hydroxy-1-oxobutyl]-2-deoxystreptamine, also known as aminotrideoxybutirosin A, and acid-addition salts. They have a wide spectrum of antibacterial activity.

The above compounds can be produced from aminodeoxybutirosin A by the sequence of reactions which comprises protecting the five primary amino groups by converting them to arylmethoxycarbonyl derivatives, converting the 3',4'-hydroxyl groups to an acetal, acylating the remaining four hydroxyl groups, and hydrolyzing the acetal to produce a key intermediate which is an O-2,6-dideoxy-2,6-bis[[(arylmethoxy)carbonyl]amino]-α-D-glucopyranosyl-(1 → 4)-O-[2,3-di-O-acyl-5-deoxy-5-[[(arylmethoxy)carbonyl]amino]-β-D-xylofuranosyl-(1 → 5)]-6-O-acyl-N¹-[(S)-2-acyloxy-1-oxo-4-[[(arylmethoxy)carbonyl]amino]-butyl]-2-deoxy-N³-[(arylmethoxy)carbonyl]streptamine, generically also identified as protected 5''-aminodeoxybutirosin A. That compound is reacted with methanesulfonyl chloride in pyridine to introduce 3',4'-methanesulfonyloxy groups which are removed by reaction with zinc and sodium iodide to introduce a double bond at the 3',4' position. The acyl groups are hydrolyzed or cleaved as by reaction with ammonia in methanol and the product is reacted with hydrogen in the presence of a catalyst to remove the arylmethoxycarbonyl groups and hydrogenate the double bond with the formation of aminotrideoxybutirosin A.

3 Claims, No Drawings

POLYAMINE COMPOUNDS AND METHODS FOR THEIR PRODUCTION

SUMMARY AND DETAILED DESCRIPTION

The present invention relates to new chemical compounds and to methods for their production. According to one aspect of the invention it relates to 0-2,6-diamino-2,3,4,6-tetradeoxy-α-D-erythro-hexopyranosyl-(1 → 4)-O-[5-amino-5-deoxy-β-D-xylofuranosyl-(1 → 5)]-N¹-[(S)-4-amino-2-hydroxy-1-oxobutyl]-2-deoxystreptamine, and to acid-addition salts thereof. According to another aspect of the invention it relates to certain chemical intermediates useful in the production of the above compounds. Those chemical intermediates include especially certain 0-2,6-dideoxy-2,6-bis[[(arylmethoxy)carbonyl]amino]-α-D-glucopyranosyl-(1 → 4)-O-[2,3-di-O-acyl-5-deoxy-5-[[(arylmethoxy)carbonyl]amino]-β-D-xylofuranosyl-(1 → 5)]-6-O-acyl-N¹-[(S)-2-acyloxy-1-oxo-4[[(arylmethoxy)carbonyl]amino]butyl]-2-deoxy-N³-[(arylmethoxy)carbonyl]streptamines.

In U.S. Pat. No. 3,541,078 there is a disclosure of a chemical product at that time called ambutyrosin (as well as its individual components ambutyrosin A and ambutyrosin B). At the present time, these substances are more commonly called butirosin (and individual components butirosin A and butirosin B), and the latter terminology is sometimes used herein.

In free base form butirosin A has the chemical structure N¹-(4-amino-2-hydroxybutyryl)-4-O-(2,6-diamino-2,6-dideoxy-D-glucopyranosyl)-5-O-D-xylofuranosyl-2-deoxystreptamine. It is also known as O-2,6-diamino-2,6-dideoxy-α-D-glucopyranosyl(1 → 4)-O-[B-D-xylofuranosyl-(1 → 5)]-N¹-[(S)-4-amino-2-hydroxy-1-oxobutyl]-2-deoxystreptamine. Butirosin A is also known in acid-addition salt forms.

5-O-(5-Amino-5-deoxy-D-xylofuranosyl)-N¹-(4-amino-2-hydroxybutyryl)-4-O-(2,6-diamino-2,6-dideoxy-D-glucopyranosyl)-2-deoxystreptamine is also known as aminodeoxybutirosin A. Another name for the same substance is O-2,6-diamino-2,6-dideoxy-α-D-glucopyranosyl-(1 → 4)-O-[5-amino-5-deoxy-β-D-xylofuranosyl-(1 → 5)]-N¹-[(S)-4-amino-2-hydroxy-1-oxobutyl]-2-deoxystreptamine.

Aminodeoxybutirosin A is conveniently synthesized from butirosin A by a procedure described in U.S. Pat. No. 3,784,541, and is the starting material to prepare the novel compounds of the present invention according to the novel procedures taught herein.

The products of the present invention can be named by systematic chemical nomenclature and also by abbreviated names which are sometimes more convenient.

O-2,6-Diamino-2,3,4,6-tetradeoxy-α-D-erythro-hexopyranosyl-(1 → 4)-O-[5-amino-5-deoxy-β-D-xylofuranosyl-(1 → 5)]-N¹-[(S)-4-amino-2-hydroxy-1-oxobutyl]-2-deoxystreptamine is also known as aminotrideoxybutirosin A. In anhydrous free base form it has the empirical formula $C_{21}H_{42}N_6O_9$, and the structural formula

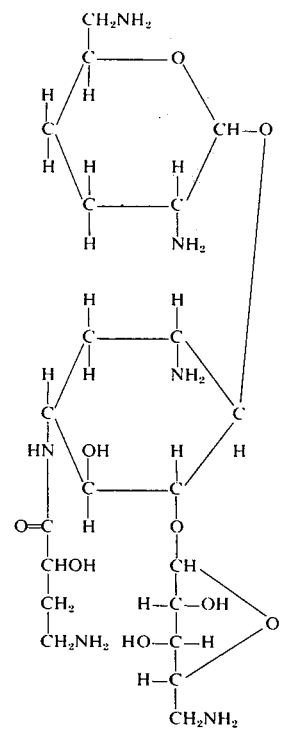

The structural formula for aminotrideoxybutirosin A can also be written as follows.

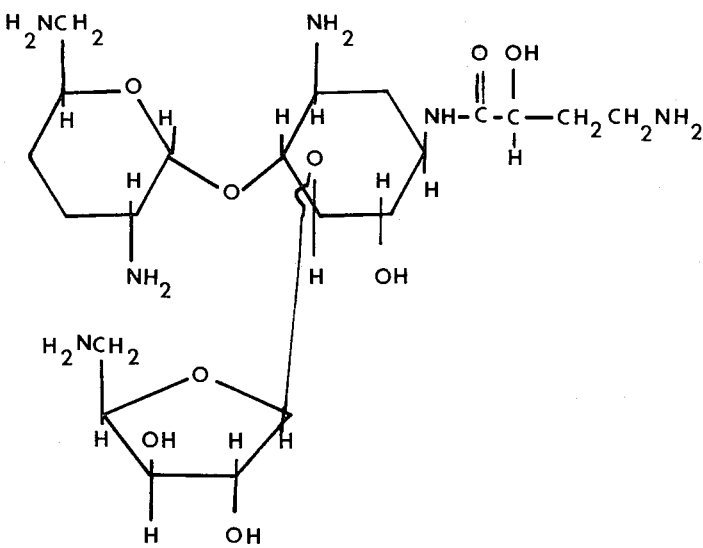

O-2,6-Dideoxy-2,6-bis[[(phenylmethoxy)carbonyl-]amino]-α-D-glucopyranosyl-(1 → 4)-0-[2,3-di-O-acetyl-5-deoxy-5-[[(phenylmethoxy)carbonyl]amino]-β-D-xylofuranosyl-(1 → 5)]-6-O-acetyl-$N^1$-[(S)-2-acetyloxy-1-oxo-4-[[(phenylmethoxy)carbonyl-]amino]butyl]-2-deoxy-$N^3$-[(phenylmethoxy)carbonyl]streptamine is also known as 2'',2''',3'',6-tetra-0-acetyl-5''-amino-penta-N-carbobenzoxy-5''-deoxybutirosin A. It is the preferred species of the group of compounds identified herein as protected 5''-aminodeoxybutirosin A. Such compounds have the structural formula

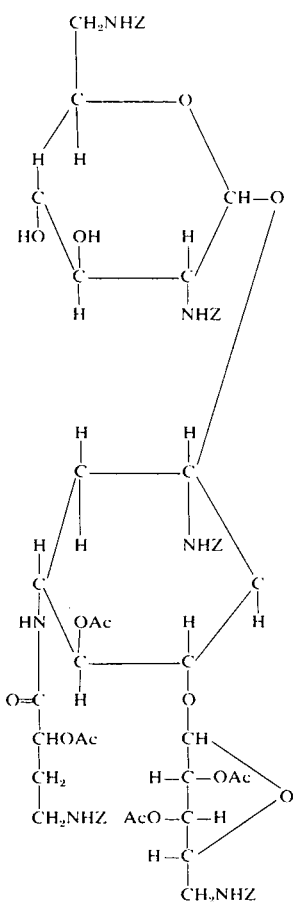

where Z is arylmethoxycarbonyl and Ac is an acyl group. For example, Z can be (phenylmethoxy)carbonyl (also known as carbobenzoxy) or substituted (phenylmethoxy)carbonyl such as (p-bromophenylmethoxy)carbonyl, (p-nitrophenylmethoxy)carbonyl, or (p-methoxyphenylmethoxy)carbonyl. Ac can be lower alkanoyl (preferably having one to three carbon atoms), substituted lower alkanoyl, benzoyl, or substituted benzoyl.

In accordance with the invention, aminotrideoxybutirosin A can be produced by reacting a compound of the formula

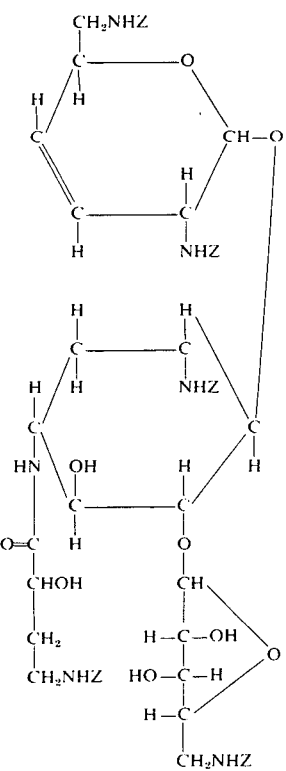

with hydrogen in the presence of a hydrogenation catalyst, and isolating the product as a free base or as an acidaddition salt; where Z is as defined before. The reaction proceeds with hydrogenation of the cyclic double bond and removal of the protective group Z from the five primary amino groups. Some examples of catalysts suitable for use in the reaction are noble metal catalysts such as platinum or palladium or oxides thereof, optionally supported on a carrier such as charcoal or barium sulfate. A preferred catalyst is palladium on charcoal. The hydrogen pressure is not critical and hydrogen at 1–3 atmospheres pressure would normally be used, or the hydrogen can simply be bubbled through the reaction mixture. Sufficient hydrogen is used to reduce the cyclic double bond and to convert the five —NHZ groups to primary amino groups. Some suitable solvents for the reaction are water miscible non-reactive solvents. These include lower alkanoic acids, lower alkanols, tetrahydrofuran, dioxane and mixtures of these. A preferred solvent is a methanol-acetic acid mixture. The presence of an acid in the reaction mixture is useful so that the progress of the reaction can be measured by carbon dioxide evolution, indicating cleavage of the —NHZ groups. The time and temperature of the reaction are not critical and it is convenient to carry out the hydrogenation at room temperature until, under acid conditions, carbon dioxide evolution is complete and there is no further uptake of hydrogen. The product is isolated as the free base or as an acid-addition salt by adjustment of the pH if required.

Aminotrideozybutirosin A forms acid-addition salts with any of a variety of inorganic and organic acids. Pharmaceutically-acceptable acid-addition salts are formed with such acids as hydrochloric, hydrobromic, sulfuric, phosphoric, acetic, succinic, citric, maleic, malic, carbonic, gluconic, pamoic and related acids.

The invention includes acid-addition salts generally as any toxic salt can be converted to the free base or to a pharmaceutically-acceptable salt. The free base and the acid-addition salt forms are interconvertible by adjustment of the pH or by the use of ion-exchange resins. They differ in solubility properties, but except as noted above are otherwise equivalent for purposes of the invention.

Aminotrideoxybutirosin A and its acid-addition salts can exist in anhydrous form as well as in solvated, including hydrated, forms. In general, the hydrated forms and the solvated forms with pharmaceutically-acceptable solvents are equivalent to the anhydrous or unsolvated form for the purposes of the invention.

Aminotrideoxybutirosin A and its acid-addition salts posses antibacterial activity. They show activity when tested by well-recognized in vitro antibacterial screening procedures. The following table shows typical results obtained from such procedures expressed in terms of the minimal concentration (measured as micrograms of free base equivalent per milliliter of Tryptic Soy broth test medium) required to inhibit the growth of each of a number of representative bacterial species. Where more than a single strain of test organism is indicated an average or approximate minimal inhibitory concentration is given.

| Microorganism | Minimal Inhibitory Concentrations, micrograms/ml. | |
|---|---|---|
| | Aminotrideoxy-butirosin A | Butirosin |
| Enterobacter cloacae (1 strain) | 6.3 | 6.3 |
| Klebsiella pneumoniae (1 strain) | 6.3 | 6.3 |
| Pseudomonas aeruginosa (6 strains) | 3.6 | 19.8 |
| Serratia marcescens (1 strain) | 12.5 | 25 |
| Staphylococcus aureus* (1 strain) | 3.1 | 50 |
| Pseudomonas aeruginosa Aquilar* (1 strain) | 6.3 | >200 |
| Escherichia coli (1 strain) | 12.5 | >200 |

*Butirosin resistant strain

Thus, aminotrideoxybutirosin A and its acid-addition salts are of value for their antibacterial activity against a number of microorganisms and especially against *Pseudomonas aeruginosa* and certain microorganisms resistant to butirosin. They can be administered either parenterally or topically. They can also be used to sterilize the gastrointestinal tract by oral administration.

Because of their wide antibacterial spectrum, the compounds of the invention are also useful as antibacterial agents in in vitro applications such as sterilizing laboratory instruments and surfaces, sterilizing pharmaceutical products, and maintaining sterile conditions during pharmaceutical manufacturing operations. For sterilizing laboratory instruments and surfaces and similar in vitro applications, the compounds can be used in the form of a 0.1 to 1.0% aqueous solution.

Starting materials and intermediates required for use in the production of aminotrideoxybutirosin A and its acid-addition salts can be prepared by any of a number of methods. For example, they can be prepared from aminodeoxybutirosin A by the sequence of reactions which comprises protecting the five primary amino groups by converting them to arylmethoxycarbonyl derivatives, converting the 3',4'-hydroxyl groups to an acetal (ketal), acylating the remaining four hydroxyl groups, and hydrolyzing the acetal to produce a key intermediate which is an O-2,6-dideoxy-2,6-bis[[(arylmethoxy)carbonyl]amino]-α-D-glucopyranosyl-(1 → 4)-O-[2,3-di-O-acyl-5-deoxy-5-[[(arylmethoxy)carbonyl]amino]-β-D-xylofuranosyl-(1 → 5)]-6-O-acyl-N$^1$-[(S)-2-acyloxy-1-oxo-4-[[(arylmethoxy)carbonyl]amino]butyl]-2-deoxy-N$^3$-[(arylmethoxy)carbonyl]streptamine, generically also identified as protected 5''-aminodeoxybutirosin A. That compound is reacted with methanesulfonyl chloride in pyridine to induce 3', 4'-methanesulfonyloxy groups which are removed by reaction with zinc and sodium iodide to introduce a double bond at the 3',4' position. The acyl groups are hydrolyzed or cleaved as by reaction with ammonia in methanol to produce the starting material directly convertible to aminotrideoxybutirosin A and acid-addition salts by catalytic hydrogenation according to the foregoing process of the invention.

Also, and more specifically, in accordance with the invention, the new chemical compounds which are the key intermediates identified above as protected 5''-aminodeoxybutirosin A can be produced by reacting an acetal of the formula

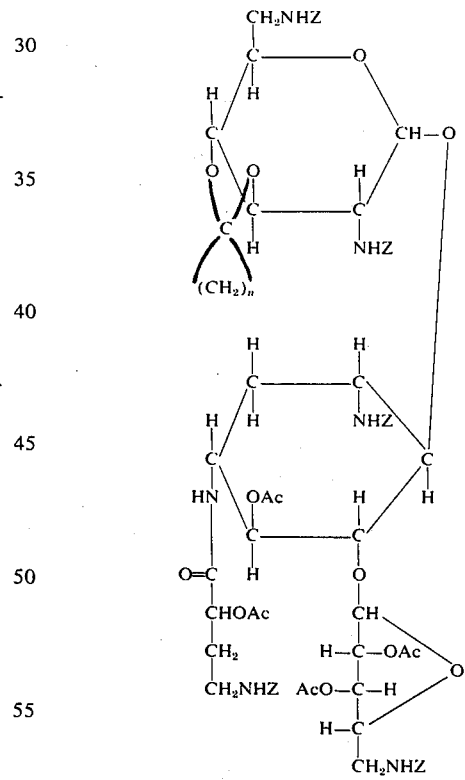

with dilute aqueous acid whereby the acetal group is hydrolyzed and hydroxyl groups are generated at positions 3' and 4'; where Z and Ac are as defined before and n is 4, 5, 6, or 7. Some suitable acid sources are weak organic acids such as lower alkanoic acids or very dilute strong organic acids or very dilute mineral acids. Strongly acid conditions are avoided. Some examples of suitable solvents are aqueous, water miscible solvents such as lower alkanoic acids, lower alkanols, dioxane, tetrahydrofuran, acetone, acetonitrile and mixtures of these. Enough water should be present to complete the hydrolysis of the 3',4'-cycloalkylidene group. A preferred reaction medium is aqueous acetic acid which functions both as the solvent and the acid. The time and temperature of the reaction are not particularly critical and it is preferred to carry out the reaction at a temperature below 50°C., for example at room temperature. The time required will depend on the temperature and on the strength of the acid used. The formation of the product as the reaction proceeds can be followed by thin layer chromatography.

The invention is illustrated by the following examples.

EXAMPLE 1

The starting material is 5''-amino-penta-N-carbobenzoxy-3',4',5''-trideoxybutirosin-3',4'-ene A, which is the compound of a foregoing formula having a double bond at positions 3', 4' and in which Z represents (phenylmethoxy)carbonyl (also known as carbobenzoxy). A slurry of 38.8 mg. of 20% palladium on charcoal in 2 ml of methanol is added to a solution of 175 mg. of 5''-aminopenta-N-carbobenzoxy-3',4',5''-trideoxybutirosin-3',4'-ene A in 6 ml. of methanol and 2 ml. of 2N acetic acid. The mixture is stirred at room temperature while hydrogen is bubbled through it for 2.5 hours. An additional 35.4 mg. of 20% palladium on charcoal suspended in 3 ml. of methanol and 2 ml. of 2N acetic acid is added and hydrogen is bubbled through the mixture for 5 hours with stirring. The resulting mixture is filtered and the filtrate is evaporated at reduced pressure. The residue is dissolved in 5 ml. of water and the solution is added to a column of 5 ml. of a weak cation exchange resin (IRC-50) in the ammonium form. The column is washed with 60 ml. of water, then eluted successively with: a) 50 ml. of 0.25M aqueous ammonia; b) 50 ml. of 0.5M aqueous ammonia; c) 50 ml. of 1M aqueous ammonia; and d) 40 ml. of 1M aqueous ammonia. The eluate from c) is evaporated at reduced pressure, then freeze-dried to give a residue of aminotrideoxybutirosin A which is obtained as a monocarbonate salt, sesquihydrate.

Thin layer chromatography (1:1 15N aqueous ammonia-methanol) on silica gel plate (Quanta Q1F, 10 cm. length) showed one major spot, Rf = 0.54.

Aminotrideoxybutirosin A is obtained in free base form by careful treatment of the monocarbonate salt with an anion exchange resin in free base form. The anhydrous form is obtained by drying in high vacuum.

Aminotrideoxybutirosin A is also known as 5''-amino-3',4',5''-trideoxybutirosin A and can be further identified by the systematic chemical nomenclature employed elsewhere herein.

EXAMPLE 2

With stirring, 0.8 ml. of water is added to a solution of 491 mg. of 2'',2''',3'',6-tetra-O-acetyl-5''-amino-penta-N-carbobenzoxy-3',4'-O-cyclohexylidene-5''-deoxybutirosin A in 3.2 ml. of glacial acetic acid. (The starting material identified is the compound of a foregoing formula in which Z is (phenylmethoxy)carbonyl, Ac is acetyl and $n$ is 5.) The mixture is allowed to stand at 20°–30°C. for 4.7 hours, then evaporated at reduced pressure to give a residue of 2'',2''', 3'',6-tetra-O-acetyl-5''-amino-penta-N-carbobenzoxy-5''-deoxybutirosin A which is dried at reduced pressure over potassium hydroxide.

Thin layer chromatography (3% methanol in chloroform) on silica gel plate (Quanta Q1F, 10 cm. length) showed one major spot, Rf = 0.28. The observed melting range was 69°–112°C. Infrared absorption maxima in a potassium bromide disc were observed at: 605, 700, 740, 778, 915, 1030 (shoulder), 1043, 1068 (shoulder), 1135, 1240, 1308, 1342, 1375, 1458, 1500 (shoulder), 1532, 1588, 1710, 1745 (shoulder), 2945, 3035, 3068, 3092, 3360–3430. Optical rotations as 1.03% solution in methanol were determined as follows:

| $\lambda$ | 589 | 578 | 546 | 436 | 365 |
|---|---|---|---|---|---|
| $[\alpha]^{23}$ | +16.9 | +17.5 | +19.8 | +34.2 | +54.7 |

STARTING MATERIALS

For convenience and clarity, various chemical intermediates referred to in this section are identified by the "butirosin" terminology as explained elsewhere herein.

To a stirred solution of 5.006 g. of aminodeoxybutirosin A in 18.75 ml. of water at 0°C. is added 35 ml. of methanol, followed by 10.111 g. of sodium bicarbonate. The mixture is stirred in an ice-water bath which 12.0 ml. of benzyl chloroformate (95%) is added dropwise during 30 minutes in 1 ml. portions, each portion being followed by 5 ml. of cold methanol. The mixture is stirred an additional 5 hours at 5°C., then treated dropwise with 6.0 ml. of pentylamine and stirred at 5°C. for 16 hours. A solution of 3.0 ml. of acetic acid in 13.5 ml. of methanol is then added slowly and the mixture is filtered, the filter cake being washed with methanol. The filtrate and washings are combined and evaporated at reduced pressure. The residual oil is triturated several times with ether, then dissolved in 150 ml. of chloroform. The chloroform solution is washed several times with water, dried and evaporated to give 5''-amino-penta-N-carbobenzoxy-5''-deoxybutirosin A. Thin layer chromatography (10% methanol in chloroform) on silica gel plate (Quanta Q1F, 10 cm. length) showed one major spot, Rf = 0.50.

To a solution of 2.692 g. of 5''-amino-penta-N carbobenzoxy-5''-deoxybutirosin A in 27 ml. of dry dimethylformamide, in a round bottom flask with a side-arm, is added 160 mg. of p-toluenesulfonic acid monohydrate and 2.0 ml. of 1,1-dimethoxycyclohexane. The flask is fitted with a coil condenser, the top of which is connected through a stopcock to a vacuum of 15 mm. Hg. The side-arm is fitted with a very fine capillary through which dry air is allowed to bubble into the solution. with the system at 15 mm. Hg pressure, the flask is heated at 50°C. for 34 minutes, then allowed to stand at room temperature for 10 minutes. The vacuum is removed and, after 40 minutes, 0.5 ml. of triethylamine is added. The mixture is evaporated at reduced pressure and the residue is dissolved in 9 ml. of chloroform. The chloroform solution is chromatographed on a column of silica gel (54 g., 1.9 cm. × 44 cm.) packed in chloroform. The column is eluted in sequence with the following solvents: (1.) 190 ml. of chloroform; (2) 200 ml. of 1% methanol in chloroform; (3) 200 ml. of 2% methanol in chloroform; (4) 200 ml. of 4% methanol in chloroform; (5) 200 ml. of 6% methanol in chloroform; (6) 250 ml. of 8% methanol in chloroform; and (7) 250 ml. of 12% methanol in chloroform. The eluate is collected in fractions of about 20 ml. each. Those fractions showing a single spot of Rf 0.65 by thin layer chromatography (silica gel plate — Quanta Q1F, 10 cm. length), using 10% methanol in chloroform, are combined and evaporated at reduced pressure to give a residue of 5''-amino-penta-N-carbobenzoxy-3',4''-O-cyclohexylidene-5''-deoxybutirosin A.

A solution of 417 mg. of 5''-amino-penta-N-carbobenzoxy-3',4'-O-cyclohexylidene-5''-deoxybutirosin A in 3.2 ml. of pyridine and 0.8 ml. of acetic anhydride is allowed to stand at room temperature for 23 hours, then evaporated at reduced pressure. The residue of 2'',2''', 3'',6-tetra-O-acetyl-5''-amino-penta-N-carbobenzoxy-3',4'-O-cyclohexylidene-5''-deoxybutirosin A is dried at reduced pressure over potassium hydroxide. That compounds is converted as described in Example 2 herein to 2'',2''',3'',6-tetra-O-acetyl-5''-aminopenta-N-carbobenzoxy-5''-deoxybutirosin A.

To a solution of 427 mg. of 2'',2''',3'',6-tetra-O-acetyl-5''-amino-penta-N-carbobenzoxy-5''-deoxybutirosin A in 5.3 ml. of dry pyridine cooled to 0°–5°C. is added with stirring 0.18 ml. of methanesulfonyl chloride. The solution is allowed to stand at room temperature for 48 hours, then treated with 0.2 ml. of water and evaporated at reduced pressure. The residue is dissolved in 40 ml. of chloroform and the solution is washed four times with 4 ml. portions of water, dried and evaporated at reduced pressure. This crude residual product, 478 mg., is combined with 316 mg. of similar material prepared from other runs, dissolved in 5 ml. of chloroform, and the solution is chromatographed on a column of silica gel (14.9 g., 1.4 cm. × 27 cm.) packed in chloroform. The column is eluted successively with: (a) 70 ml. of chloroform; (b) 70 ml. of 0.5% methanol in chloroform; and (c) 165 ml. of 1.0% methanol in chloroform. The eluate is collected in fractions of about 3 ml. each. Those fractions showing a single spot of Rf 0.48 by thin layer chromatography (silica gel plate, Quanta Q1F, 10 cm. length), using 3% methanol in chloroform, are combined and evaporated at reduced pressure to give a residue of 2'',2''',3'',6-tetra-O-acetyl-5''-amino-penta-N-carbobenzoxy-5''-deoxy-3',4'-di-O-methanesulfonylbutirosin A.

To a solution of 180.4 mg. of 2'',2''',3'',6-tetra-O-acetyl-5''-amino-penta-N-carbobenzoxy-5''-deoxy-3',4'-di-O-methanesulfonylbutirosin A in 3.6 ml. of dry dimethylformamide is added 228 mg. of Linde Molecular Sieve Type 3A (or a similar material), 1.836 g. of dry sodium iodide and 922.8 mg. of zinc dust. The mixture is stirred and heated at 90°C. for 1.5 hours, cooled, diluted with 25 ml. of chloroform and filtered through infusorial earth (Celite). The filter cake is washed with 10 ml. and 5 ml. portions of chloroform. The filtrate and washings are combined and washed successively with 20 ml. of water, two 5 ml. portions of saturated aqueous sodium thiosulfate and three 10 ml. portions of water. The chloroform solution is dried and evaporated at reduced pressure to give a residual oil. This crude oily product (570 mg. from two similar preparations) is dissolved in 7.5 ml. of chloroform and the solution is chromatographed on a column of silica gel (17.12 g., 1.5 cm. × 29 cm.) packed in chloroform. The column is eluted successively with: (a) 50 ml. of chloroform; (b) 50 ml. of 0.5% methanol in chloroform; (c) 50 ml. of 0.75% methanol in chloroform; (d) 50 ml. of 0.85% methanol in chloroform; (e) 130 ml. of 1% methanol in chloroform; (f) 100 ml. of 1.5% methanol in chloroform; and (g) 100 ml. of 2.5% methanol in chloroform. The eluate is collected in fractions of about 6 ml. each. Those fractions showing a single spot of Rf 0.42 by thin layer chromatography (silica gel plate, Quanta Q1F, 10 cm. length), using 2.5% methanol in chloroform, are combined and evaporated at reduced pressure to give a residue of 2'',2''',3'',6-tetra-O-acetyl-5''-amino-penta-N-carbobenzoxy3',4',5''-trideoxybutirosin-3',4'-ene A.

Ammonia gas is bubbled into a solution of 140 mg. of 2'',2''',3'',6-tetra-O-acetyl-5''-amino-penta-N-carbobenzoxy-3',4',5''-trideoxybutirosin-3',4'-ene A in 5 ml. of methanol at 0°C. for 4 minutes. The resulting solution is kept at 4°C. for 7 hours, aerated with nitrogen and evaporated at reduced pressure to give a residue of 5''-amino-penta-N-carbobenzoxy-3',4',5''-trideoxybutirosin-3',4'-ene A.

Thin layer chromatography (8% methanol in chloroform) on silica gel plate (Quanta Q1F, 10 cm. length) showed one major spot, Rf = 0.30.

I claim:
1. A member of the class consisting of O-2,6-diamino-2,3,4,6-tetradeoxy-α-D-erythro-hexopyranosyl-(1 → 4)-O-[5-amino-5-deoxy-β-D-xylofuranosyl-(1 → 5)]-N$^1$-[(S)-4-amino-2-hydroxy-1-oxobutyl]-2-deoxystreptamine and pharmaceutically acceptable salts thereof.

2. A compound of the formula

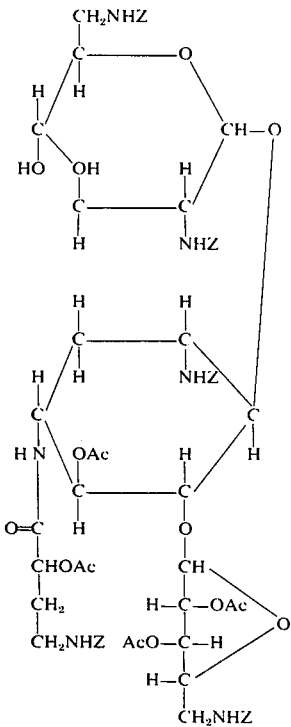

where Z is (phenylmethoxy)carbonyl or substituted (phenylmethoxy)carbonyl, and Ac is a lower alkanoyl group of from one to three carbon atoms.

3. A compound according to claim 2 where Z is (phenylmethoxy)carbonyl and Ac is acetyl.

* * * * *

UNITED STATES PATENT AND TRADEMARK OFFICE
CERTIFICATE OF CORRECTION

PATENT NO. : 3,960,837

DATED : June 1, 1976

INVENTOR(S) : Peter Wing Kee Woo

Page 1 of 3

It is certified that error appears in the above-identified patent and that said Letters Patent are hereby corrected as shown below:

Column 3, amend formula to read:
(Only partial formula, lines 15-30 involving correction, is shown)

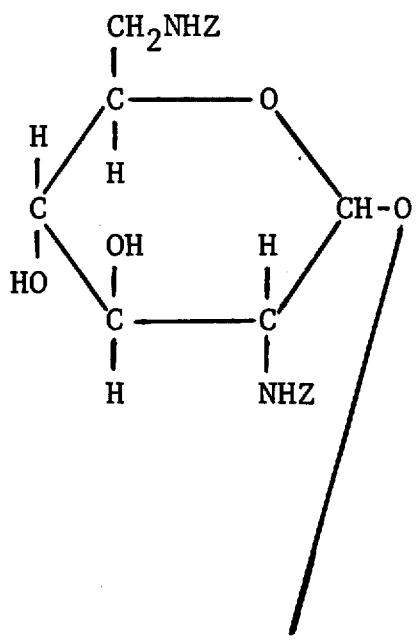

UNITED STATES PATENT AND TRADEMARK OFFICE
CERTIFICATE OF CORRECTION

PATENT NO. : 3,960,837
DATED : June 1, 1976
INVENTOR(S) : Peter Wing Kee Woo

It is certified that error appears in the above-identified patent and that said Letters Patent are hereby corrected as shown below:

Column 4, amend formula to read:
(Only partial formula, lines 12-22 involving correction, is shown)

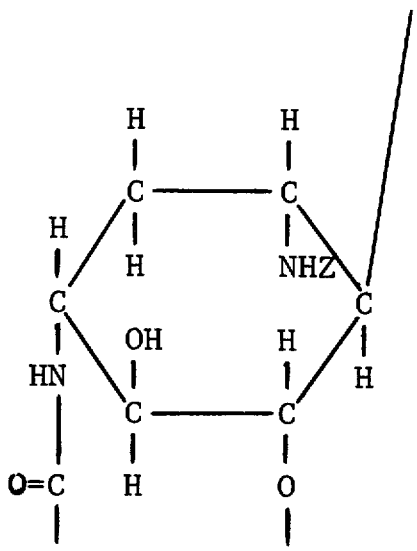

UNITED STATES PATENT AND TRADEMARK OFFICE
CERTIFICATE OF CORRECTION

PATENT NO. : 3,960,837
DATED : June 1, 1976
INVENTOR(S) : Peter Wing Kee Woo

It is certified that error appears in the above-identified patent and that said Letters Patent are hereby corrected as shown below:

Column 10, amend formula to read:
(Only partial formula, lines 32-41 involving correction, is shown)

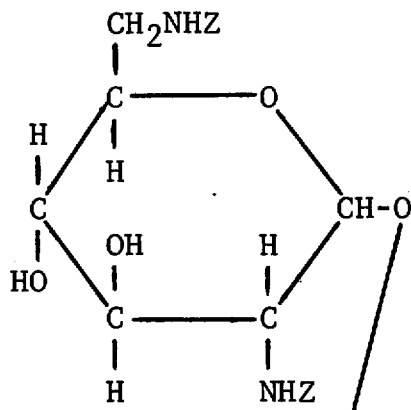

Signed and Sealed this

Twelfth Day of April 1977

[SEAL]

Attest:

RUTH C. MASON
*Attesting Officer*

C. MARSHALL DANN
*Commissioner of Patents and Trademarks*